(12) United States Patent
Quaggin

(10) Patent No.: US 9,719,135 B2
(45) Date of Patent: Aug. 1, 2017

(54) CONDITIONAL ANGIOPOIETIN-1/ANGIOPOIETIN-2 DOUBLE KNOCK-OUT MICE WITH DEFECTIVE OCULAR DRAINAGE SYSTEM

(71) Applicant: MANNIN RESEARCH INC, Toronto (CA)

(72) Inventor: Susan E. Quaggin, Chicago, IL (US)

(73) Assignee: MANNIN RESEARCH INC., Toronto, Ontario (CA)

( * ) Notice: Subject to any disclaimer, the term of this patent is extended or adjusted under 35 U.S.C. 154(b) by 0 days.

(21) Appl. No.: 14/790,884

(22) Filed: Jul. 2, 2015

(65) Prior Publication Data

US 2016/0000871 A1    Jan. 7, 2016

Related U.S. Application Data

(60) Provisional application No. 62/020,868, filed on Jul. 3, 2014.

(51) Int. Cl.
*A01K 67/027* (2006.01)
*A61K 49/00* (2006.01)
*C12Q 1/68* (2006.01)
*A61K 9/00* (2006.01)
*A61K 38/18* (2006.01)
*C07K 14/515* (2006.01)

(52) U.S. Cl.
CPC .......... *C12Q 1/686* (2013.01); *A01K 67/0276* (2013.01); *A61K 9/0048* (2013.01); *A61K 38/1891* (2013.01); *A61K 49/0008* (2013.01); *C12Q 1/6883* (2013.01); *A61K 9/0019* (2013.01); *C07K 14/515* (2013.01)

(58) Field of Classification Search
None
See application file for complete search history.

(56) References Cited

U.S. PATENT DOCUMENTS

2009/0226447 A1* 9/2009 Boone .................... C07K 16/22
424/139.1

OTHER PUBLICATIONS

Shen et al, 2014. Arterioscler Thromb Vasc Biol: 1221-1230; published on-line Apr. 24, 2014.*
UCDavis KOMP Repository Knockout Mouse Project order page available at https://www.komp.org/vectorOrder. php?projectid=CSD49726; 1 page as printed; printed on Apr. 15, 2016.*
Guan et al, 2010. Genesis. 48: 73-85.*

* cited by examiner

*Primary Examiner* — Zachary Howard
(74) *Attorney, Agent, or Firm* — Finnegan, Henderson, Farabow, Garrett & Dunner, L.L.P.

(57) ABSTRACT

This invention relates to the production and genotyping of mice lacking both Angiopoietin 1 and Angiopoietin 2. This invention also relates to the use of Tie2 receptor activation for treatment of open angle glaucoma, congenital glaucoma and cystic kidney disease, and more specifically to the use of angiopoietin 1 recombinant proteins, peptides, VE-PTP phosphatase inhibitors, and Tie2— peptomimetics to improve lymphatic drainage in the Schlemm's canal and corneal limbal lymphatic system for open angle glaucoma and congenital glaucoma patients, and to slow and/or reduce the growth of cysts in patients with cystic kidney disease.

2 Claims, 8 Drawing Sheets

```
SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caatgccaga ggttcttgtg aa                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcaaagcaac atatcatgtg ca                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatgccaga ggttcttgtg aa                                              22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtgagcaaa acccctttc                                                  19
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggaaacctc aacactccaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acaccggcct ctagacacac                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaggcgcata acgataccac                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgagaactct gcagccttga                                              20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acactgtcct cccaacagct tctt                                         24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgattcgatt gccatccaac gcac                                         24

<210> SEQ ID NO 11
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caaatgctgg accaaacaca                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgccatccag ccattcagtc                                              20
```

CONDITIONAL ANGIOPOIETIN-1/ANGIOPOIETIN-2 DOUBLE KNOCK-OUT MICE WITH DEFECTIVE OCULAR DRAINAGE SYSTEM

SEQUENCE LISTING

The instant application contains a Sequence Listing which has been submitted electronically in ASCII format and is hereby incorporated by reference in its entirety. Said ASCII copy, created on Sep. 16, 2015, is named 127325-387871_SL.txt and is 2,965 bytes in size.

FIELD OF THE INVENTION

This invention relates to the use of Tie2 receptor activation for treatment of open angle glaucoma, congenital glaucoma and cystic kidney disease, and more specifically to the use of angiopoietin 1 recombinant proteins, peptides, VE-PTP phosphatase inhibitors, and Tie2- peptomimetics to improve lymphatic drainage in the Schlemm's canal and corneal limbal lymphatic system for open angle glaucoma and congenital glaucoma patients, and to slow and/or reduce the growth of cysts in patients with cystic kidney disease.

BACKGROUND OF THE INVENTION

The Angiopoietin-Tie2 signaling pathway is a major regulator of vascular development, and altered expression of the Angiopoietin ligands or activity of the Tie2 receptor has been linked to a variety of vascular diseases and adverse outcomes in patients. In blood vascular endothelium, Angiopoietin2 is reported to function as a competitive antagonist of Angiopietin1/Tie2 signaling, inhibiting Angiopoietin1-mediated phosphorylation of Tie2.

Pharmaceuticals with agents which inhibit or modify kinases and therefore inhibit vascular development are used for treatment of some types of cancer as well as other diseases, such as neovascular glaucoma, abnormal ocular vasculatures and glaucoma generally as set out in U.S. Pat. Nos. 8,754,209, 8,529,943, 8,476,434, 8,450,305, 8,425,469, and 8,338,455; and U.S. patent application Ser. Nos. 14/119,532, 13/920,103, 14/131,024, and 13/652,154 (U.S. Patent Application Publication Nos. 2014/0161720, 2014/0004175, 2014/0163079, and 2013/0095105, respectively), each of which is hereby incorporated by reference in its entirety.

Knowledge of pathways regulating vascular development has been used to develop drugs for controlling this development. Knowledge of pathogenetic and molecular pathways leading to disease conditions can reveal methods of treating or preventing such conditions. For example, increased intraocular pressure (TOP) due to impaired aqueous humor drainage is a major risk factor for development of glaucoma, and determining the pathway by which this occurs would be helpful in finding other treatments. Glaucoma is a leading cause of blindness, afflicting more than 60 million people worldwide.

Although inhibitory kinases haves been used to treat glaucoma, particularly neovascular glaucoma, there is a need to know the pathway that is active and leads to open angle glaucoma and congenital glaucoma in order to provide better treatment and prevention of this condition.

SUMMARY OF THE INVENTION

Embodiments of the invention include a method of treating a patient having open angle glaucoma, congenital glaucoma or cystic kidney disease by administering a pharmaceutical composition comprising agents capable of TIE2 receptor activation. Embodiments of the invention include a method of treating a patient having open angle glaucoma, congenital glaucoma or cystic kidney disease comprising administering a pharmaceutical composition comprising one or more of angiopoietin 1 recombinant proteins, peptides, VE-PTP phosphatase inhibitors, and Tie2- peptomimetics.

In embodiments, the invention includes the use of a pharmaceutical composition comprising one or more of angiopoietin 1 recombinant proteins, peptides, VE-PTP phosphatase inhibitors and Tie2- peptomimetics for improving ocular lymphatic drainage. In embodiments, the invention includes the use of a pharmaceutical composition comprising one or more of angiopoietin 1 recombinant proteins, peptides, VE-PTP phosphatase inhibitors and Tie2- peptomimetics for improving drainage through Schlemm's canal and corneal limbal lymphatics.

In embodiments the invention is a pharmaceutical composition for topical delivery to the eye comprising an effective dosage amount of Tie2 receptor activating agents. Embodiments of the invention include a pharmaceutical composition comprising a pharmaceutically active amount of Tie2 receptor activating agents and a pharmaceutically acceptable carrier for topical delivery to the eye. The pharmaceutically acceptable carrier can be a controlled release vehicle, selected from the group consisting of biocompatible polymers, other polymeric matrices, capsules, microcapsules, nanocapsules, microparticles, nanoparticles, microspheres, bolus preparations, osmotic pumps, diffusion devices, liposomes, lipospheres.

In embodiments, the invention is a conditional Angiopoeitin 2 knockout allele. Embodiments of the invention also include the use of a conditional Angiopoeitin 2 knockout allele to produce mice lacking Angiopoeitin 2.

The invention also includes use of the following primers for PCR genotyping of mice: AngptlFlox, Forward 5'-CAATGCCAGAGGTTCTTGTGAA-3' (SEQ ID NO: 1); Reverse 5'-TCAAAGCAACATATCATGTGCA-3' (SEQ ID NO: 2) (WT: 233bp product, AngptlFlox: 328bp), Angpt1Delete, Forward 5'-CAATGCCAGAGGTTCTTGT-GAA-3' (SEQ ID NO: 3); Reverse 5'-TGTGAGCAAAAC-CCCTTTC-3' (SEQ ID NO: 4) (431bp product), Angpt2Flox, Forward 5'-GGGAAACCTCAACACTC-CAA-3' (SEQ ID NO: 5); Reverse 5'-ACACCGGCCTCTA-GACACAC-3' (SEQ ID NO: 6) (WT:224bp product, Angpt2Flox: 258bp) and Angpt2Delete, Forward 5'-AAGGCGCATAACGATACCAC-3' (SEQ ID NO: 7); and Reverse 5'-TGAGAACTCTGCAGCCTTGA-3' (SEQ ID NO: 8) (Angpt2Flox: 1,372bp product, Angpt2Delete: 426bp).

The invention also includes a pharmaceutical composition for subcutaneous delivery comprising an effective dosage amount of Tie2 receptor activating agents for treatment of cystic kidney disease. The invention also includes a pharmaceutical composition comprising a pharmaceutically active amount of Tie2 receptor activating agents and a pharmaceutically acceptable carrier for subcutaneous delivery for treatment of cystic kidney disease.

BRIEF DESCRIPTION OF THE FIGURES

These and other aspects of the present invention will be apparent from the brief description of the drawings and the following detailed description in which.

DESCRIPTION

Figure 1:
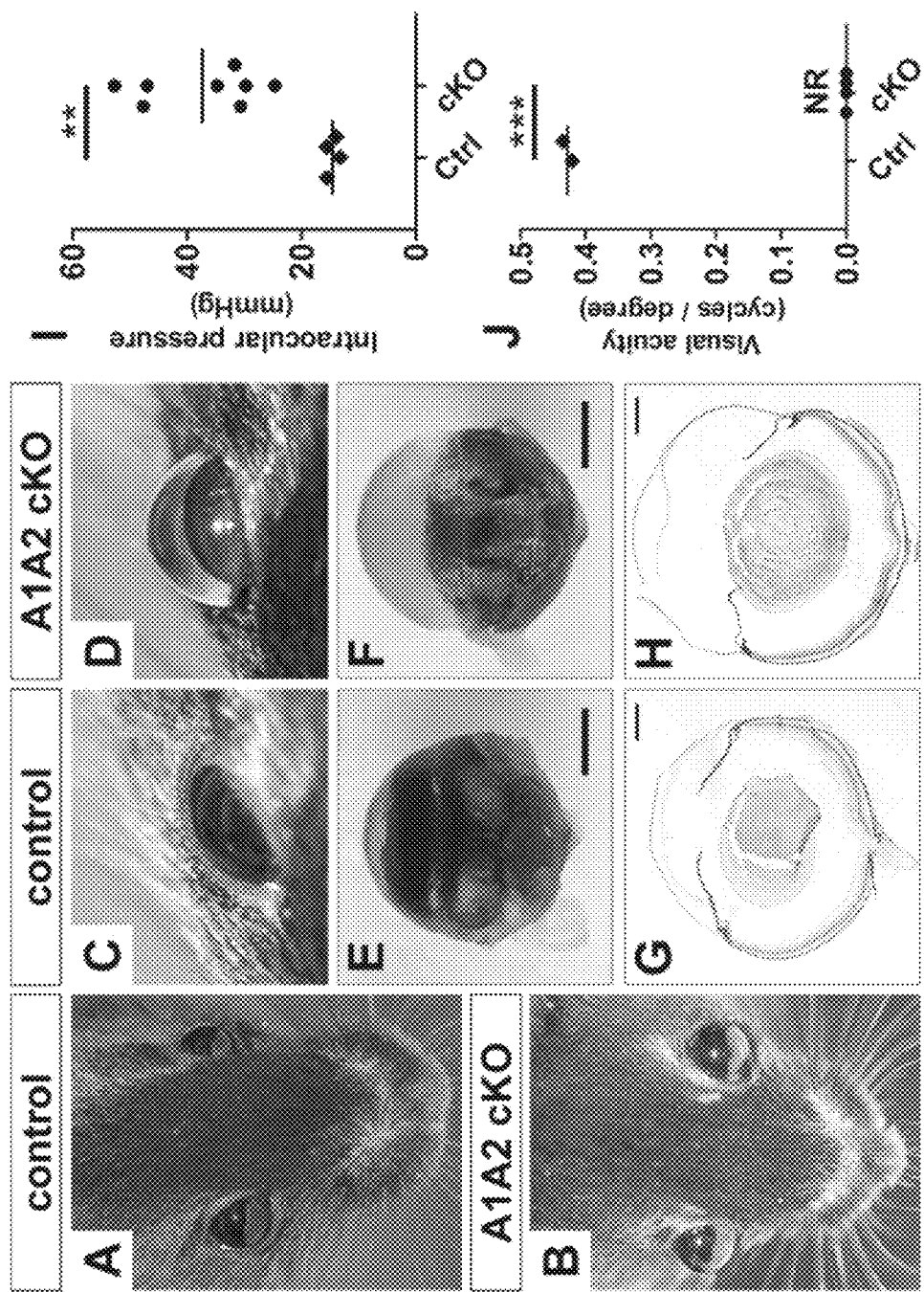
FIG. 1 shows A1A2Flox$^{WB\Delta E16.5}$ (cKO) mice develop bilateral buphthalmos. While control eyes (a,c,e,g) appear normal, 8-week old A1A2Flox$^{WB\Delta E16.5}$ mice (b,d,f,h) show enlargement of the anterior chamber due to increased intraocular pressure (i). Optomotor response tests (j) show impaired vision in mutant animals. Scale bars represent 1 mm (e,f) and 500 μM (g,h). Error bars indicate s.e.m. *P<0.05, P<0.01,*P<0.001 determined by two-tailed t test. NR (no response) indicates an optomotor response of <0.042 cycles/degree.

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Angiopoeitin2 ("Angpt2") and the orphan receptor Tie1 are known to be involved in lymphatic development, but until now, roles for Tie2 and its canonical ligand Angpt1 have not been described. Surprisingly, while Angiopoietin ("Angpt1") knock out ("KO") mice die between E9.5 and E12.5 due to major cardiovascular defects, conditional deletion of Angpt1 after E13.5 produces no overt vascular phenotypes in adult mice.

However, while the blood vascular role of the pathway has been extensively studied, the function of angiopoietins in lymphatic endothelium is uncertain.

To determine if there is unrecognized cooperation between Angpt1 and Angpt2 in vivo, which might provide compensation in mice lacking Angpt1, a conditional Angpt2 knockout allele was generated and produced mice lacking both major Angiopoietin ligands (A1A2Flox$^{WB}$). Strikingly, simultaneous deletion of both ligands at midgestation phenocopies deletion of Tie2—demonstrating cooperativity between Angpt1 and Angpt2 in vivo. Whole-body deletion of the Tie2 receptor or both Angpt1 and Angpt2 at E12.5 leads to gross subcutaneous edema in embryos, with associated patterning defects in dermal lymphatic vessels. While Angpt2 knockout mice exhibit lymphatic valve defects and mesenteric lymphatic abnormalities resulting in chylous ascites (2), they do not develop the embryonic edema observed in A1A2Flox$^{WB}$ or Tie2 conditional KO mice, suggesting a compensatory role for Angpt1 in lymphatic development.

Deletion of the Tie2/Tek ligands angiopoietin 1 and 2 in mice (A1A2Flox$^{WB}$ mice) results in high IOP, bupthalmos and classic features of glaucoma including retinal ganglion degeneration and vision loss. Eyes from A1A2Flox$^{WB}$ mice lack drainage pathways including Schlemm's canal and lymphatic capillaries in the corneal limbus, which share expression of Prox1, VEGFR3, and the Foxc transcription factors that are linked to glaucoma and lymphatic disorders in patients. In contrast to blood endothelium where Angpt2 is an antagonist of Angpt1, it is shown that both ligands cooperate to regulate Tie2 in the lymphatic network of the eye. While A1A2Flox$^{WB}$ mice develop high IOP and glaucoma, expression of Angpt1 or Angpt2 alone is sufficient for ocular drainage. Furthermore, it is demonstrated that loss of Foxc2 from lymphatics results in Tie2 downregulation, suggesting a mechanism for ocular defects in patients with Foxc mutations. These data reveal a new pathogenetic and molecular basis for glaucoma, demonstrating the importance of angiopoietin ligand cooperation in lymphatic endothelium.

Figure 2:
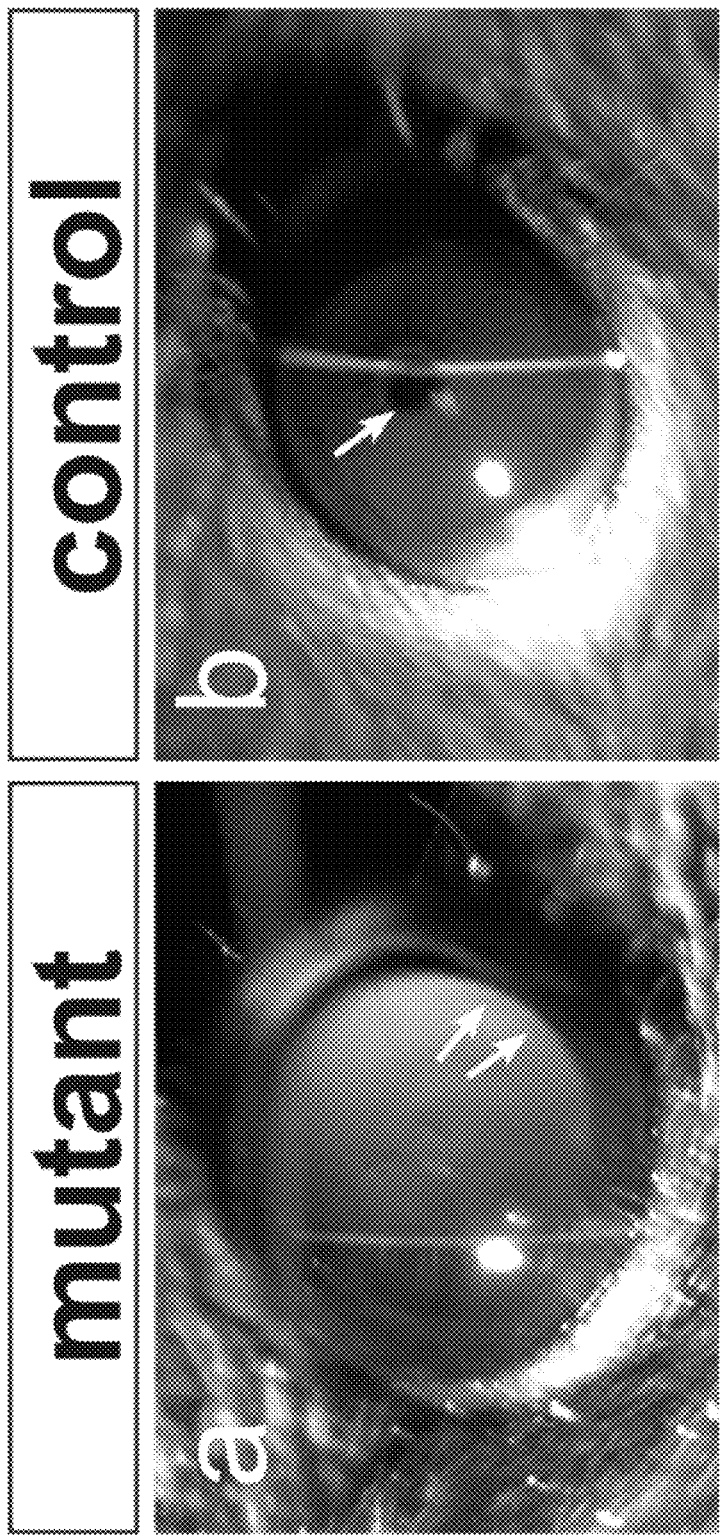
FIG. 2 shows slit lamp photography shows marked pupil dilation in A1A2Flox$^{WB\Delta E16.5}$ mice (a) compared to a control littermate (b) at 8 weeks of age. Pupil edge is indicated by arrows.
Figure 3:
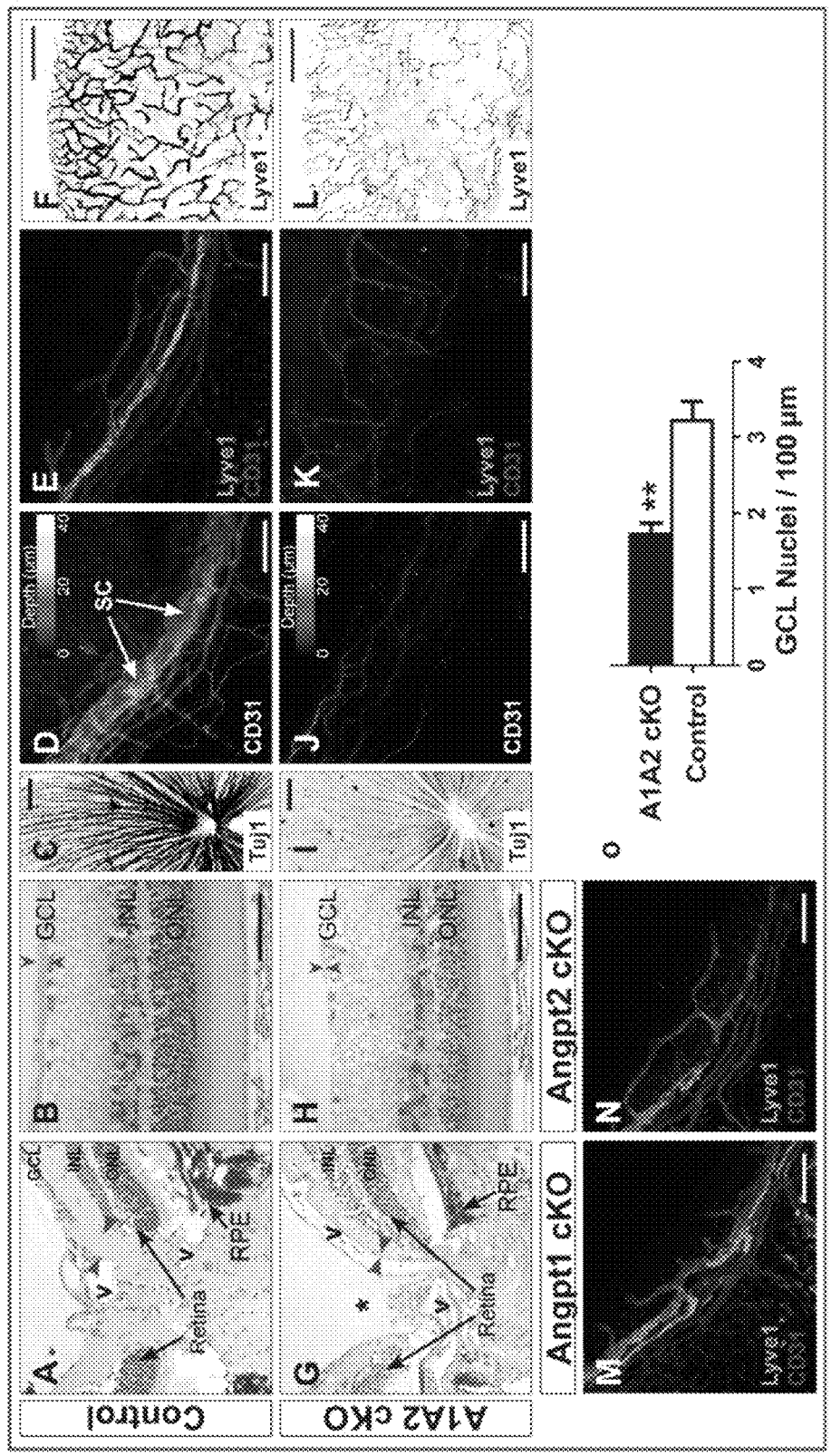
FIG. 3 shows A1A2Flox$^{WB\Delta E16.5}$ mice develop glaucoma due to defects in ocular drainage. Compared to controls (a), the optic nerve head appears abnormal in A1A2Flox$^{WB\Delta E16.5}$ mice (g), with thinning of the nerve fiber layer (red arrowheads) and optic nerve excavation (asterisk). Semi-thin sections show thinning of the nerve fiber, ganglion, and nuclear cell layers in the central retina (b,h). Loss of nerve fibers is confirmed by Tuj1 staining (c,i). Unlike littermate controls (d), Schlemm's canal is absent in A1A2 cKO mice (j). Anterior chamber drainage is further diminished by a loss of Lyve-1 positive lymphatic capillaries in the corneal limbus (e,k). Lymphatic vasculature is present in non-ocular tissues, but exhibits disturbed patterning as shown here in the dermis of the ear (f1). Mice lacking Angpt1 or Angpt2 individually develop lymphatics in the corneal limbus (m,n). Compared to controls, A1A2 cKO mice have fewer nuclei in the retinal ganglion cell layer (o). GCL, ganglion cell layer, INL, inner nuclear layer, ONL, outer nuclear layer, RPE, retinal pigment epithelium, V, blood vessel, SC, Schlemm's canal. Red arrowheads indicate thickness of the nerve fiber layer. Scale bars indicate 200 μm in all panels except f and 1 where they represent 1 mm. **P<0.01.
Figure 4:
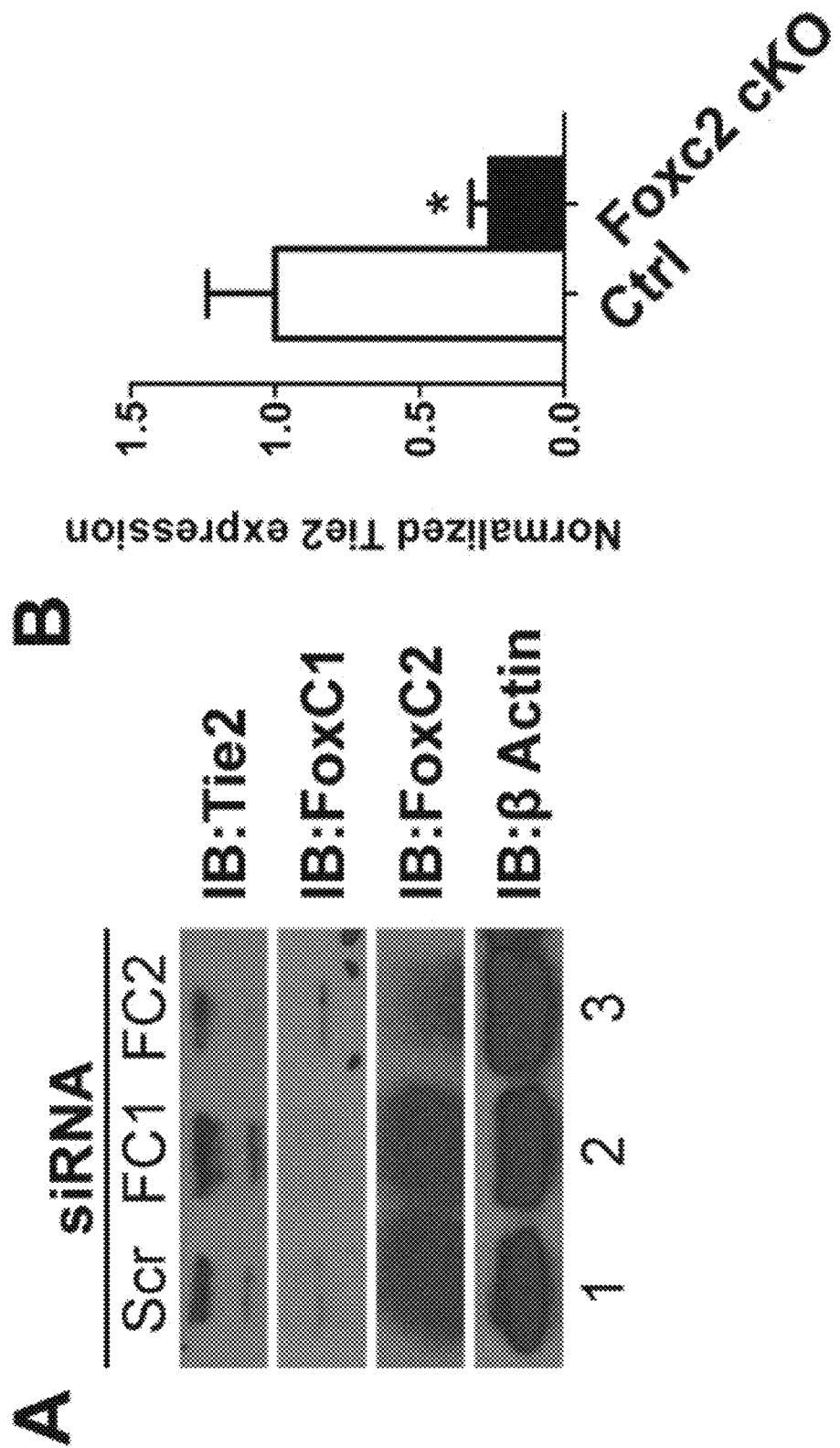
FIG. 4 shows Foxc2 regulates Tie2 expression in lymphatic endothelium. (a) Tie2 mRNA expression was measured by real-time PCR in lymphatic endothelial cells isolated from E15.5 Foxc2$^{FLox/Flox}$ (Ctrl) or Foxc2$^{flox/flox}$; Prox1CreERT2 (Foxc2 cKO) mouse embryos. N=6 control and 6 Foxc2 cKO embryos. (b) Human dermal lymphatic endothelial cells were cultured in the presence of specific siRNAs targeting Foxc1, Foxc2 or a scrambled siRNA control. Compared to scrambled control siRNA (lane 1) or Foxc1 siRNA (lane 2), siRNA targeting Foxc2 (lane 3) caused a reduction in Tie2 protein expression. Error bars indicate s.e.m. *P<0.05 determined by two-tailed t test.

To investigate combined role(s) of Angiopoietin 1 and 2 in adult mice, both ligands were deleted at E16.5. A1A2Flox$^{WB\Delta E16.5}$ mice are born in normal Mendelian numbers and are indistinguishable from control littermates during the first 3 weeks of life. However, eyes of mutant animals begin to protrude noticeably 21-28 days after birth. As shown in FIGS. 1 a to d, bilateral buphthalmos worsens with age, and by 8 weeks, mice have difficulty closing their eyelids. Gross examination reveals corneal enlargement and increased anterior chamber depth as is shown in FIGS. 1 e to h. Pupils of A1A2Flox$^{WB}$ mice appear fully dilated (FIG. 2), suggesting that anterior segment enlargement is due to high intraocular pressure (IOP)(9). IOP was measured at 10 weeks using a rebound tonometer(10). While control animals had intraocular pressure readings within the normal range, IOP of mutant littermates was significantly elevated, ranging from 24-52 mmHg (FIG. 1 i). Using an optomotor response test(11, 12) A1A2Flox$^{WB\Delta E16.5}$ mice were found to have severely impaired vision, with visual acuity <0.042 cycles/degree in all animals examined (FIG. 1 j). Histological analysis of eye sections revealed excavation of the optic nerve head (FIG. 3 a,g) and other characteristic features of glaucomatous eye disease. Mutant retinas have reductions in thickness of retinal cell layers including the ganglion and inner nuclear layers and loss of the nerve fiber layer (FIG. 3 b,c,h,i,o; FIGS. 3,4). Unlike human glaucoma, which is rarely associated with photoreceptor loss (13), A1A2Flox$^{WB\Delta E16.5}$ mice show thinning of the outer nuclear layer which worsens toward the retinal periphery. This outer retina damage is similar to that described in laser-induced models of high-IOP mouse glaucoma, suggesting the possibility of pressure-related or ischemic effects (14). While loss of photoreceptors may be partially responsible for the vision loss observed, this degree of photoreceptor atrophy is not sufficient to explain the dramatic decrease in visual acuity seen in A1A2Flox cKO mice. Taken together, these data confirm that A1A2Flox$^{WB}$ mice represent a new model of glaucoma.

To determine the cause of high intraocular pressure and glaucoma in A1A2Flox$^{WB\Delta E16.5}$ mice, the aqueous humor drainage system of the eye was studied. While the trabecular meshwork and ciliary body were indistinguishable between knockouts and controls, Schlemm's canal ("SC") was absent in 8/8 A1A2Flox$^{WB\Delta E16.5}$ eyes examined (FIG. 3 e,f). SC was present in all control littermates. Although SC is a major route of aqueous humor drainage from the iridocorneal angle, defects in SC formation have not been reported to raise IOP in mice. Transgenic mice haplon sufficient for the transcription factor Foxc1 have been reported to exhibit small or absent SC, yet do not develop high IOP (15). Previous studies of aqueous humor dynamics in mice have suggested that only 20% of total fluid drainage is carried out via SC, suggesting that alternate drainage routes including the uveoscleral and lymphatic routes may be able to increase flow in compensation for defects in SC (16).

Figure 7:
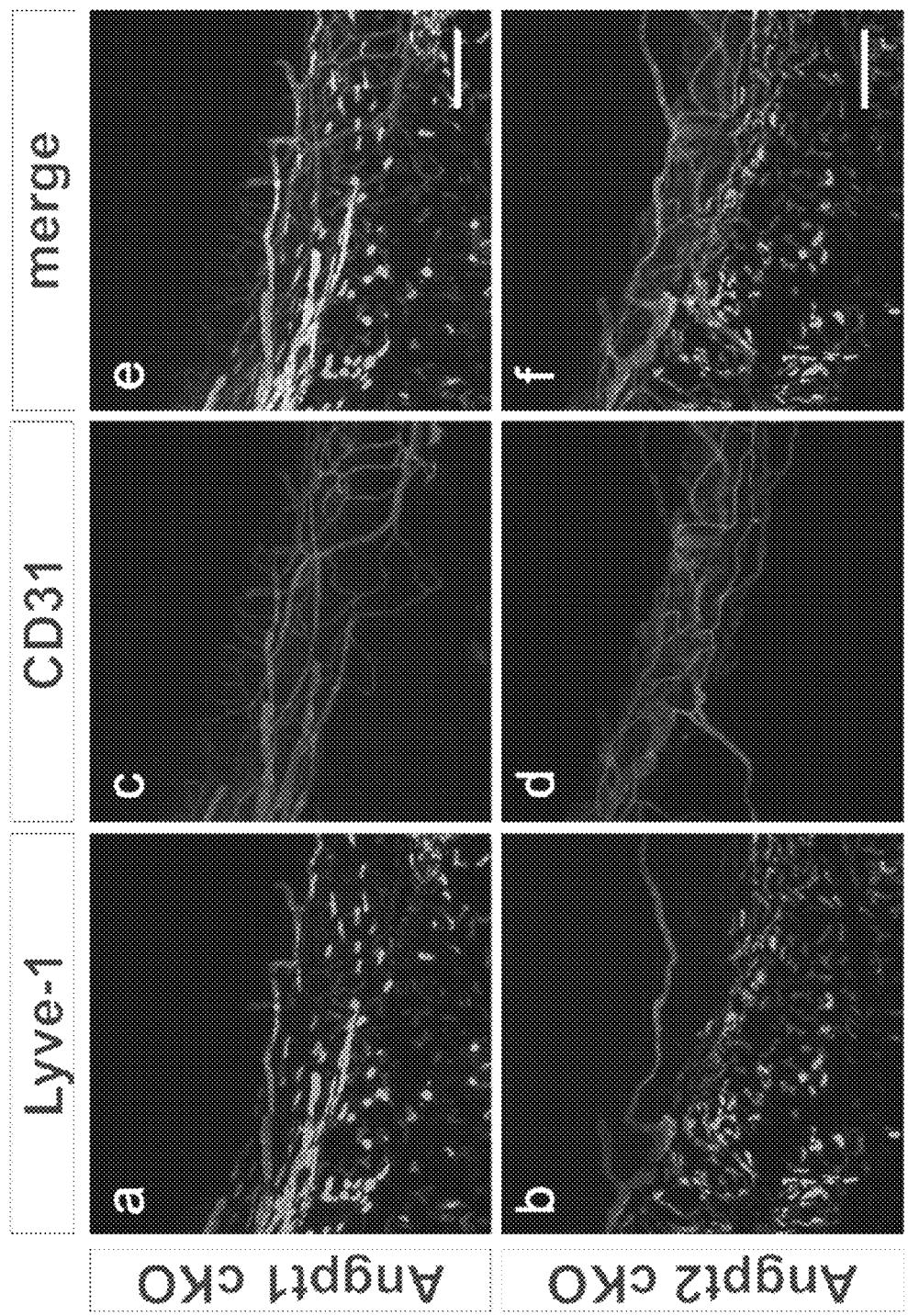
FIG. 7 shows Lyve-1-positive lymphatic (a,b) and CD31-positive vascular (c,d) capillaries develop in the corneal limbus of mice lacking either Angpt1 or Angpt2 alone. These mice do not develop the buphthalmos phenotype observed in double knockout A1A2Flox$^{WB\Delta E16.5}$ mice.

To better understand alternate drainage pathways of the anterior chamber, lymphatic and vascular capillaries in the corneal limbus were studied. Vessels were examined by confocal microscopy of flat-mounted eyes, which revealed complete absence of Lyve-1 positive lymphatic endothelium in the limbus of A1A2Flox$^{WB\Delta E16.5}$ mice (FIG. 3 e,k). By contrast, CD31-positive blood vasculature is present, but exhibits disturbed patterning, with some capillary loops extending into the cornea. It is unclear if this aberrant vascular morphology is a direct effect of Angpt1 and Angpt2 deletion, or a response to loss of lymphatic drainage and/or stretching of the cornea. Mice lacking Angpt1 or Angpt2 alone develop normal lymphatic vasculature in the corneal limbus (FIG. 3 m,n, FIG. 7), suggesting the presence of inter-ligand compensation in the lyphatic endothelium. Corneal neovascularization and glaucoma have been described in patients with Axenfeld-Rieger syndrome due to mutations in Foxc1, and Foxc1 haploinsufficient mice exhibit defects in the anterior chamber and Schlemm's canal, suggesting a link to this molecular pathway(15). Intriguingly, the downstream targets of Foxc1 responsible for these anterior chamber defects have not been elucidated. Given the matching expression pattern of Foxc1 and 2 with Tie2 and Angpt2 in lymphatics, as well as the overlapping phenotypes (18, 19), Foxc1 or Foxc2 may be responsible for regulating expression of Tie2 or angiopoietin ligands in lymphatic endothelium. De Val and colleagues have reported the presence of a FOX:ETS transcriptional enhancer sequence in the Tie2 promoter region, and demonstrated Foxc2-mediated enhancer activation using an in vitro reporter system—further suggesting a link between these pathways(20). The possibility of Foxc-mediated Tie2 regulation was investigated using complimentary in vivo and in vitro systems, at the protein and mRNA level. Lymphatic endothelial cells were isolated from lymphatic-specific Foxc2 knockout (Foxc2$^{flox/flox}$;Prox1CreERT2 (21)) embryos at embryonic day 15.5 using fluorescent activated cell sorting (FACS). mRNA was isolated, and real-time PCR revealed a 74.5% reduction (N=6 animals per group, P=0.015) in Tie2 mRNA expression relative to controls (FIG. 4 a). This result was verified at the protein level using an in vitro siRNA system in human dermal lymphatic endothelial cells. Using this system, siRNA targeting of Foxc2 was found to cause marked reduction in Tie2 protein expression compared to Foxc1 or scrambled siRNAs (FIG. 4 b).

These results suggest a mechanism for lymphatic phenotypes in patients with Foxc2 mutations or in Foxc2 knockout mice, and provide additional evidence of a connection between Foxc and angiopoietin/Tie2 molecular pathways.

Figure 5:
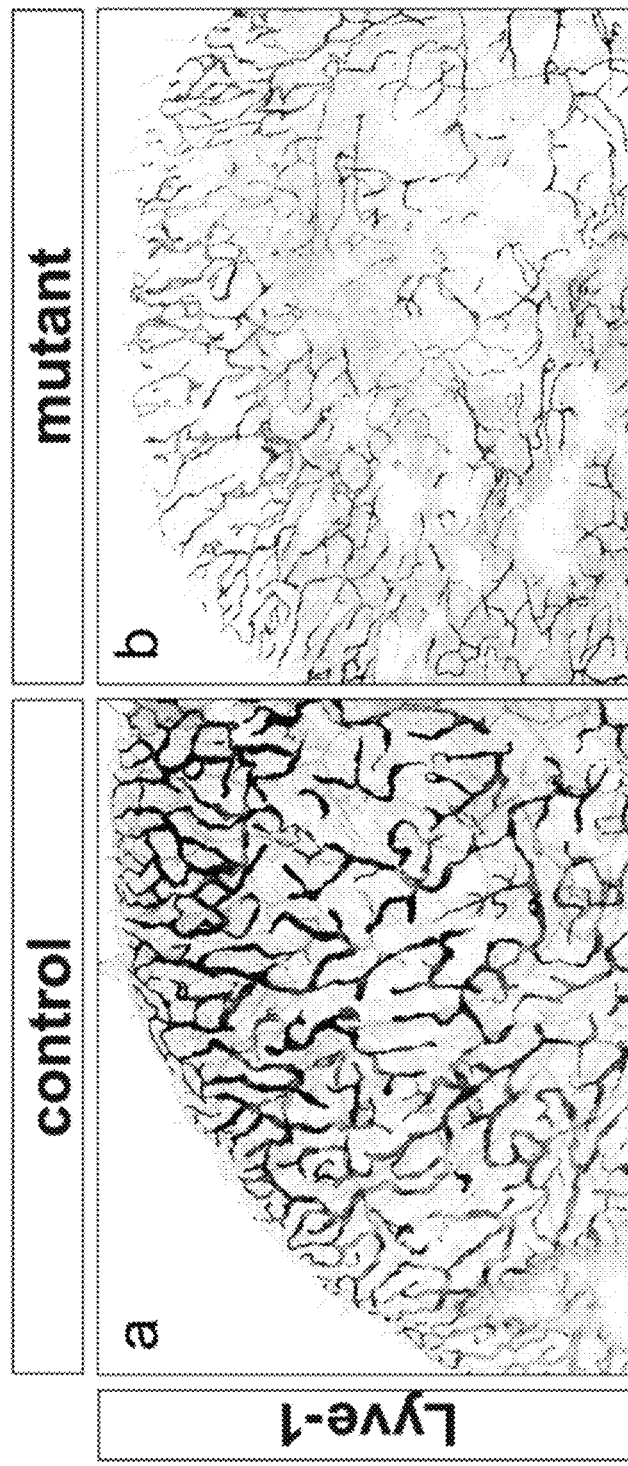
FIG. 5 shows lymphatic vessels present in extra-ocular tissues of A1A2Flox$^{WB\Delta E16.5}$ mice. Confocal microscopy was used to compare patterning of LYVE-1 positive lymphatic capillaries in whole mount ear tissue from (a) control and (b) A1A2Flox$^{WB\Delta E16.5}$ mice.
Figure 6:
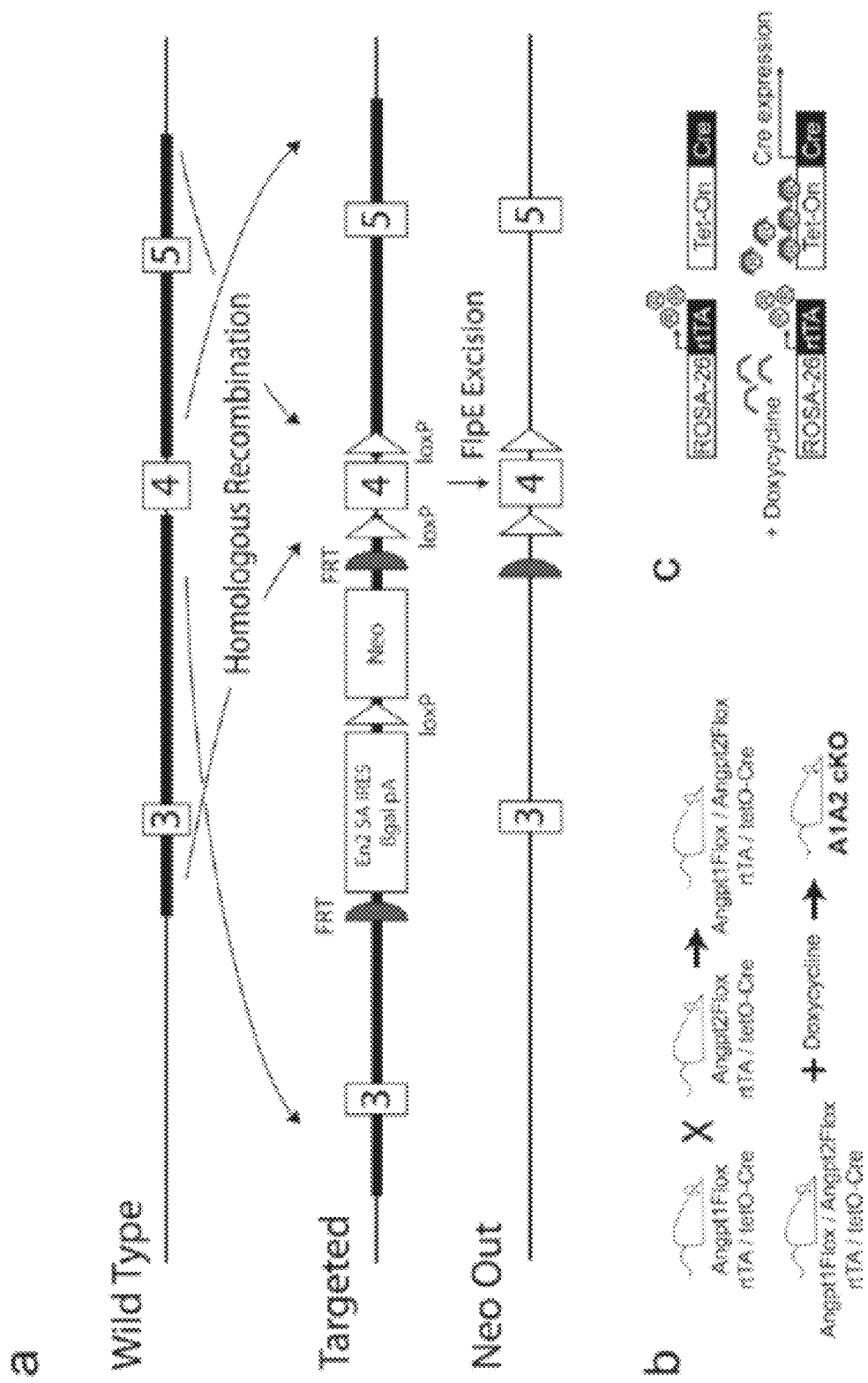
FIG. 6 shows the strategy used to generate the whole-body, inducible combined Angpt1/Angpt2 knockout mouse model (A1A2Flox$^{WB}$ mice). (a) The conditional Angpt2 knockout construct contains loxp sites flanking exon 4 and was used to target mouse embryonic stem cells. Chimeric founders were crossed to mice expressing FlpE recombinase to excise the neomycin selection cassette and produce Angpt2Flox(Neo out) mice. (b) Angpt2Flox(Neo out) mice were bred with an inducible, whole body Angpt1 knockout model to generate the A1A2Flox$^{WB}$ mice described in this study. (c) The ROSA26-rtTA-TetOnCre system allows robust, whole-body deletion of Angpt1 and Angpt2 upon induction with doxycycline.

Surprisingly, Lyve-1 positive lymphatic vessels are present in non-ocular tissues of A1A2Flox$^{WB\Delta E16.5}$ mice, although patterning in some organs is abnormal. In the dermis of the ear, lymphatic vessels appear sparse with variable vessel diameter and abnormal branching (FIG. 5 a,b) similar to that described in Angpt2-null mice (19). It is possible that the specialized lymphatic vessels of the anterior chamber are more dependent on Angpt-Tie2 signaling than other lymphatic endothelia, suggesting that, like vascular endothelia, lymphatic capillaries from different organs are heterogeneous with unique functions and regulatory mechanisms. Indeed, Schlemm's canal has been described as a hybrid vessel with features of both blood and lymphatic endothelium, expressing blood endothelial markers CD34 and E-Selectin, and a subset of lymphatic markers including Prox1 and VegfR3 but not Podoplanin (22-24).

The cardiovascular phenotypes reported in Angpt1 and Tie2 knockout models highlight the important function of these molecules in cardiac development and angiogenesis. In older animals, the data suggest Angiopoietin-Tie2 signaling is less critical in quiescent blood vasculature, but continues to play a major role in lymphatic endothelium. At the outset, it was hypothesized that A1A2Flox$^{WB}$ mice would develop severe vascular defects, revealing a compensatory role for Angpt2 in the blood vasculature of mice lacking Angpt1. Instead, it was observed that lymphatic defects reported in Angpt2-null mice are enhanced by the additional loss of Angpt1, demonstrating cooperation between ligands in lymphatic endothelium.

While the overall mechanism responsible for human glaucoma remains obscure, the most important risk factor is elevated intraocular pressure (25). IOP is determined by the relative rates of aqueous humor drainage and formation, and the majority of glaucoma treatment has focused on lowering TOP by targeting these systems (26). Aqueous humor is thought to drain through two major pathways, the trabecular meshwork leading to SC, and the uveoscleral pathway. In humans, studies have estimated that the uveoscleral pathway accounts for 46-54% of total outflow, with the remainder carried through SC (27). The contribution of lymphatic vessels to each pathway has not been reported, but recent studies in sheep have suggested they do play an important role in allowing fluid to escape from the anterior chamber (28). As increased TOP observed in A1A2Flox$^{WB\Delta E16.5}$ mice is more severe than that of other models with abnormal SC, it was hypothesized that lymphatic vessels are essential for maintaining aqueous humor flow through the uveoscleral route.

It was shown that A1A2Flox$^{WB\Delta E16.5}$ mice lack both Schlemm's canal and the lymphatic capillaries of the corneal limbus, leading to a dramatic increase in TOP and glaucoma. These data show that promotion of lymphangiogenesis with therapies such as Vegfc or Angpt-Tie2 agonists provides therapies for glaucoma.

Figure 8:
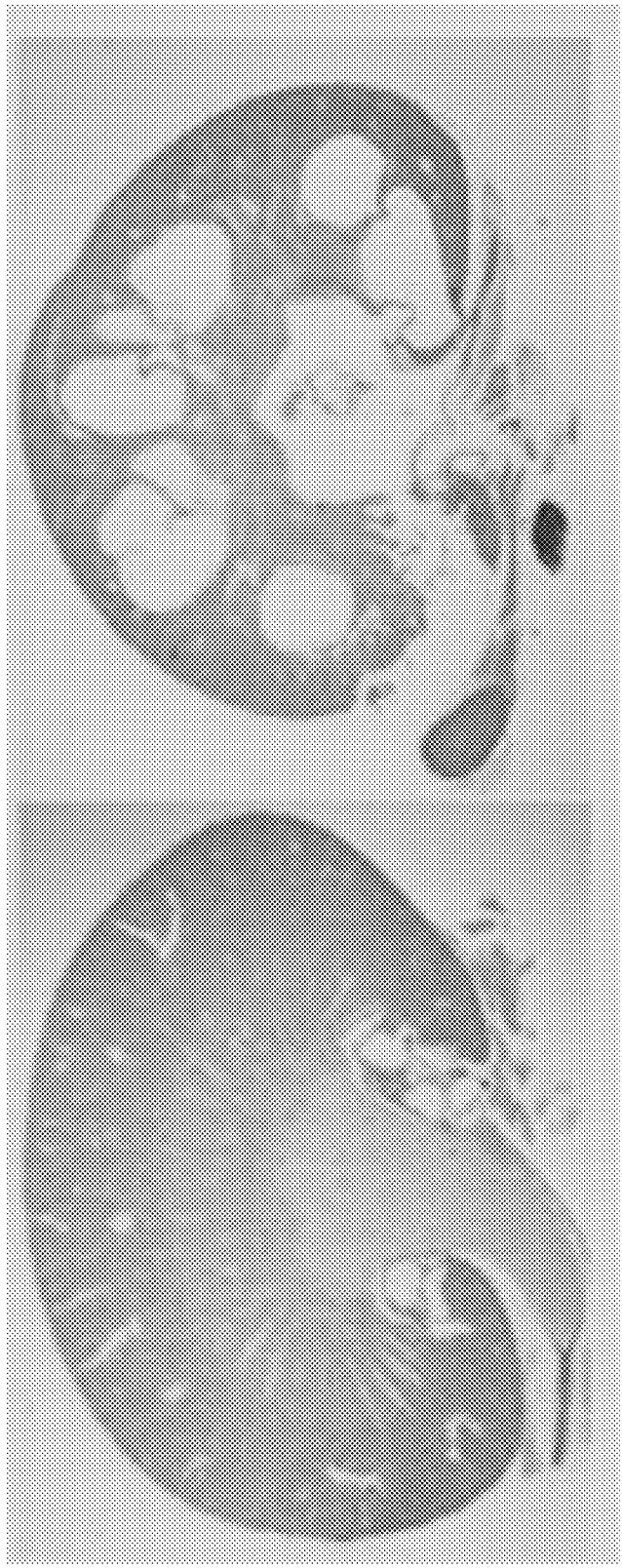
FIG. 8 shows a control kidney cross-section at left and on the right a cross-section of a A1A2Flox$^{WB\Delta E16.5}$ mouse kidney showing dramatic cysts.

It was also found that dramatic cysts are observed in mice lacking Angiopoietin 1 and 2 (FIG. 8 with A1A2Flox$^{WB\Delta E16.5}$ kidney shown on right).

Given that the A1A2Flox$^{WB\Delta E16.5}$ mice lack both Schlemm's canal and the lymphatic capillaries of the corneal limbus and also have dramatic kidney cysts, current activators of the Tie2 system will be helpful in treatments for people with open angle glaucoma and congenital glaucoma as well as those with cystic kidney disease. For patients with open angle glaucoma and congenital glaucoma Tie2 activation improves the size of Schlemm's canal and improvement of drainage, respectively. A pepto-mimic (peptide/nano-medicine) in an eye drop formulation is useful for treatment of open angle glaucoma and congenital glaucoma and the level of the resulting Tie2 activation is measurable by assessment of phosphorylation of Tie2/Tek. In glaucoma these Tie2 receptor activators can improve ocular lymphatic drainage, and specifically improve drainage through Schlemm's canal and corneal limbal lymphatics, through topical delivery of these Tie2 receptor agonists delivered to the eye.

Loss of Angpt1 and Angpt2 concurrently or their canonical receptor Tie2/Tek results in dramatic cystic formation in the kidney. Activation of Tie2 will reverse these phenotypes. Delivery of these Tie2 receptor activators is by subcutaneous injection for cystic kidney disease.

Currently available Tie2 receptor activators are: angiopoietin 1 recombinant proteins, peptides, VE-PTP phosphatase inhibitors, and Tie2– peptomimetics. However, it will be understood that new forms of Tie2 receptor activators as developed are also applicable to the present invention.

Examples Supporting FIGS. 1, 3, 4
Study Approval

All animal experiments were approved by the Animal Care Committees at the Center for Comparative Medicine of Northwestern University (Evanston, Ill., USA).
Mice and Breeding To create the doxycycline-inducible, whole-body Angpt1; Angpt2 double knockout mouse used in this study, a new Angpt2Flox mouse was generated which was crossed onto the ROSA-rtTA;Tet-On-Cre, whole-body Angpt1 knockout line previously developed in our laboratory (3). Whole-body Cre recombinase expression was induced by treating pregnant dams with doxycycline at embryonic day 16.5 (E16.5) to generate A1A2Flox$^{WB\Delta E16.5}$ pups.
Live-Animal Studies Intraocular pressure was measured at 8 weeks of age using a Tonolab rebound tonometer (iCare, Vantaa, Finland) as previously described 13. Visual acuity was estimated using an Optomotor response test14, 15. The optomotor system used for these studies provides a maximum grating size of 0.042 cycles per degree, and mice were scored as "no response" if they were unable to respond to this stimulus.
Tissue Collection and Histology A1A2Flox$^{WB}$ mice induced at E16.5 and littermate controls were aged 8 weeks before tissue harvest for histological studies. Whole eyes were perfusion-fixed (2.5% Gluteraldehyde, 2% Formaldehyde in 0.1M phosphate buffer pH 7.4), embedded in Epon 812 and sectioned using an ultramicrotome. Sections were stained with Toluine blue and imaged on a compound microscope. Optic nerve sections were embedded in paraffin, sectioned and stained using haematoxylin and eosin.
Immunofluorescence Eyes dissected from A1A2Flox$^{WB\Delta E16.5}$ mice and littermate controls were bisected and immersion fixed (4% Formaldehyde, 0.1M phosphate buffer pH 7.4). After fixation, retinas and optic nerves were removed and hemispheres stained as whole-mounts.
Fluorescent Activated Cell Sorting (FACS) and Real-Time PCR of Mouse Lymphatic Endothelial Cells Cells isolated from E15.5 control (Foxc2$^{flox/flox}$) and lymphatic-specific Foxc2 knockout (Foxc2$^{flox/flox}$; Prox1CreERT2) mouse embryos were stained for Lyve-1 and CD31 and subjected to FACS as previously described (29). RNA was extracted from sorted lymphatic endothelial cells, cDNA was synthesized and qPCR was run using an ABI 7500 real-time thermocycler.
Lymphatic Endothelial Cell Culture, siRNA Transfection, and Western Blot Human dermal lymphatic endothelial cells were cultured with fetal bovine serum, antibiotics and other supplements. Cells were transfected with Foxc1, Foxc2 or control siRNAs and incubated for 48 h. At the end of incubation, cells were harvested and lysates prepared. Proteins were separated by SDS-PAGE and blotted onto PVDF membranes for western blot.
Statistics and Figures Throughout, indicated P-values were obtained using a two-tailed Student's t-test. P-values are shown in figures using the following notation: * $P<0.05$,  $P<0.01$ and * $P<0.001$.
Examples Supporting FIGS. 2, 5, 6 and 7
Mice and Breeding All animal experiments were approved by the Animal Care Committees at the Center for Comparative Medicine of Northwestern University (Evanston Illinois, USA) and the Toronto Centre for Phenogenomics (Toronto, Ontario, Canada). Animals housed at either center were allowed unrestricted access to standard rodent chow (Harlan #7912) and water.

To create the conditional Angpt1, Angpt2 double knockout mouse line used in this study, a new Angpt2Flox mouse was generated which was crossed onto the inducible, whole-body Angpt1knockout line previously developed in our laboratory (3). An Angpt2Flox targeting construct was obtained from the Sanger Institute knockout mouse project (clone #PRPGS00100_B_CO2) and used to target mouse embryonic stem (ES) cells by homologous recombination.

This construct introduces loxp recombination sites flanking exon 4 of the Angpt2 gene, as well as a neomycin-resistance cassette flanked by frt recombination sites for flpe recombinase (FIG. 6a). Blastocyst morula aggregation was performed at the Toronto Centre for Phenogenomics (Toronto, Canada), and chimeras were crossed to wild-type ICR mice. F1 animals were screened by PCR and Southern blot, and those positive for the Angpt1Flox(Neo in) allele were crossed to mice expressing F1pE recombinase (B6;SJL-Tg (ACTFLPe)9205Dym/J, The Jackson laboratory, Bar Harbor, Maine) to excise the Neomycin selection cassette used in ES cell cloning. F1pE excision was verified by Southern blot, and Angpt2Flox(Neo out) mice were selected for all subsequent breeding. Newly created Angpt2Flox mice were crossed onto the whole-body, inducible Angpt1Flox/ROSA26-rtTA/TetOnCre line previously generated in our laboratory (3) to create Angpt1/Angpt2/ROSA26-rtTA/TetOnCre line (A1A2F1oxWB mice). Angpt1 and Angpt2 deletion was induced by addition of 0.5% Doxycycline to the drinking water of pregnant dams at day 16.5 of gestation to generate A1A2Flox$^{WB.E16.5}$ offspring. Knockout mice were genotyped by PCR, using the following primers: Angpt1Flox, Forward 5'CAATGCCAGAGGTTCTTGT-GAA-3' (SEQ ID NO: 1); Reverse 5'TCAAAGCAACATAT-CATGTGCA-3' (SEQ ID NO: 2) (WT: 233bp product, Angpt1Flox: 328bp), Angpt1Delete, Forward 5'-CAATGC-CAGAGGTTCTTGTGAA-3' (SEQ ID NO: 3); Reverse 5'-TGTGAGCAAAACCCCTTTC-3' (SEQ ID NO: 4) (431bp product), Angpt2Flox, Forward 5'-GGGAAACCT-CAACACTCCAA-3' (SEQ ID NO: 5); Reverse 5'-ACAC-CGGCCTCTAGACACAC-3' (SEQ ID NO: 6) (WT: 224bp product, Angpt2Flox: 258bp) and Angpt2Delete, Forward 5'-AAGGCGCATAACGATACCAC-3' (SEQ ID NO: 7); Reverse 5'-TGAGAACTCTGCAGCCTTGA-3' (SEQ ID NO: 8) (Angpt2Flox: 1,372bp product, Angpt2Delete: 426bp).

Live-Animal Studies

Intraocular pressure was measured at 8 weeks of age using a Tonolab rebound tonometer (iCare, Vantaa, Finland). Mice were restrained in a soft plastic cone and ocular pressure for each eye was averaged from three sets of six recordings. Each mouse was measured on two subsequent days and the results were averaged to obtain the reported IOP values. Visual acuity was measured using an Optomotor response test as previously described (10, 12). Briefly, animals were placed on an elevated platform surrounded by four LCD monitors. Monitors displayed vertical gratings as moving visual stimuli. Mice were observed and head movement following the direction of moving gratings was scored as positive optomotor response. Spatial frequency of the moving gratings was gradually increased, and visual acuity was scored as the highest frequency triggering a response. Optomotor tests on each mouse were repeated on consecutive days, and results for each mouse were averaged to obtain the final visual acuity value. The optomotor response system used for these studies provides a maximum grating size of 0.042 cycles per degree, and mice were scored as "no response" if they were unable to respond to this stimulus. For statistical comparison, animals with no optomotor response were assigned a score of 0.042 c/d.

Tissue Collection and Histology

A1A2Flox$^{WB}$ mice induced at E16.5 (A1A2Flox$^{WB.E16.5}$) and littermate controls were aged 8 weeks before tissue harvest for histological studies. Mice were anesthetized by i.p. injection with 2, 2, 2-Tribromoethanol. Tissues were cleared (PBS, 1 mg/ml lidocaine, 10u/ml heparin) and fixed (2.5% Gluteraldehyde, 2% Formaldehyde in 0.1M phosphate buffer pH 7.4) by cardiac perfusion. Eyes were dissected and postfixed for an additional 8 hours at 4°. Whole eyes were embedded in Epon 812 and 0.5 μM sections were prepared. Sections were stained with Toluine blue and imaged on a compound microscope. Histological studies were performed using groups of 4 mice per genotype, and several sections were examined from each animal.

Immunofluorescence

A1A2Flox$^{WB.E16.5}$ mice and littermate controls were sacrificed following anesthesia by i.p. injection of 2, 2, 2-Tribromoethanol. Eyes were dissected and immersion fixed (4% Formaldehyde, 0.1M phosphate buffer pH 7.4). For flat mounts, fixed eyes were bisected sagittally, retinas and optic nerves were removed and hemispheres stained as wholemounts.

Samples were blocked overnight (5% Donkey serum, 0.5% Triton X100, TBS pH 7.4) before incubation with appropriate primary and fluorochrome-labeled secondary antibodies (Invitrogen, Carlsbad, Calif.). Stained tissues were flat-mounted and imaged using a Nikon C2+ confocal microscope. Due to the thickness of whole-mount limbus tissue, 30 μM Z-stacks were collected and maximum intensity projections were used in the present manuscript. Primary antibodies used: goat anti-mouse Lyve-1 (R&D Systems AF2125), rat anti-mouse CD31 (BD Pharmingen 550274).

Fluorescent Activated Cell Sorting (FACS) and Real-Time PCR of Mouse Lymphatic Endothelial Cells Cells isolated from E15.5 control (Foxc2$^{flox/flox}$) and lymphatic-specific Foxc2 knockout (Foxc2$^{flox/flox}$; Prox1CreERT2) mouse embryos were stained for Lyve-1 and CD31 and subjected to FACS as previously described (29). Briefly, E15.5 embryos were harvested in Hank's balanced salt solution (HBSS, Sigma-Aldrich) and then chopped for an overnight digestion with collagenase I/II. The colleagenase-treated cell suspension was incubated with RBC (Red blood cell) lysis buffer (StemCell Technologies, Vancouver, Canada). Following centrifugation, cell pellets were incubated with anti-Lyve-1 antibody (Abcam) for 20 min at 40C. After washing with PBS, the cells were then stained with PE conjugated anti-CD31 antibody (BD Pharmingen) and Alexa 488-conjugated donkey anti-rabbit secondary antibody (Invitrogen, Carlsbad, CA). After gauze filtration with a cell strainer (40μm BD Biosciences) to obtain a single cell suspension, Lyve-1+/CD31+LECs were sorted using BD FacsAria SORP 4-Laser. RNA was extracted from sorted LEC using TriZol (Invitrogen), cDNA was synthesized using the cDNA synthesis kit (Biorad) according to manufacturer's instructions. qPCR was run using an ABI 7500 real-time thermocycler using the following primers: Tie2Fwd: 5'-ACACTGTCCTCCCAACAGCTTCTT-3' (SEQ ID NO: 9), Tie2Rev: 5'-TGATTCGATTGCCATC-CAACGCAC-3' (SEQ ID NO: 10), PpiaFwd: 5'CAAAT-GCTGGACCAAACACA-3' (SEQ ID NO: 11), PpiaRev: 5'TGCCATCCAGCCATTCAGTC-3' (SEQ ID NO: 12).

Lymphatic Endothelial Cell Culture, siRNA Transfection, Protein Extract Preparation and Western Blot Human dermal lymphatic endothelial cells were cultured in EBM media (LONZA, Basel, Switzerland) with 10% fetal bovine serum, antibiotics and other supplements. The cells were transfected with Foxc1, Foxc2 or control siRNAs using Lipofectamine RNAiMAX (Invitrogen) and incubated for 48 h. At the end of incubation, cells were harvested and whole cell lysates were prepared using RIPA buffer. Protein lysates were separated by SDS-PAGE and blotted onto PVDF membranes (Bio-Rad). Membranes were blocked (TBS with 5% donkey serum, 2.5% BSA, 0.05% Tween-20)

and incubated with appropriate primary and HRP-tagged secondary (Jackson Immunoresearch) antibodies. Signals were detected using ECL reagents (Bio-Rad). siRNAs: Scrambled (Qiagen, #1027281), Foxc1 (Thermo Scientific, #L-009318-00-0005), Foxc2 (Thermo Scientific #ATTAA-004016). Primary antibodies: Rabbit anti-mouse Tie2 (Santa Cruz #SC-324, reported by the supplier to recognize Tie2 of human and mouse origin), Rabbit anti-mouse 13Actin (Abcam #ab8227), Sheep anti-human FoxC2 (R&D Systems #AF5044).

Statistics and Figures

Throughout this study, plotted values are shown as means+/−standard error (SEM). Statistical comparisons were performed using Graphpad Prism 5.0 (Graphpad Software Inc. San Diego, Calif.). Indicated P-values were obtained using a two-tailed Student's t-test unless otherwise noted in the manuscript. P-values were indicated in figures using the following notation: * $P<0.05$,  $P<0.01$ and * $P<0.001$. Figures were assembled using Graphpad Prism 5.0, Photoshop CS5 (Adobe Software, San Jose Calif.) and InDesign CS5 (Adobe Software).

From the above detailed description of the invention, the operation and construction of same should be apparent. While there are herein shown and described example embodiments of the invention, it is nevertheless understood that various changes may be made with respect thereto without departing from the principle and scope of the invention as measured by the following claims.

REFERENCES

Each of the following references below is hereby incorporated by reference in the entirety.

1. Dumont DJ, Gradwohl G, Fong GH, Puri MC, Gertsenstein M, Auerbach A, and Breitman ML. Dominant-negative and targeted null mutations in the endothelial receptor tyrosine kinase, tek, reveal a critical role in vasculogenesis of the embryo. *Genes & Development*. 1994; 8(16):1897-909.
2. Gale NW, Thurston G, Hackett SF, Renard R, Wang Q, McClain J, Martin C, Witte C, Witte MH, Jackson D, et al. Angiopoietin-2 Is Required for Postnatal Angiogenesis and Lymphatic Patterning, and Only the Latter Role Is Rescued by Angiopoietin-1. *Developmental Cell*. 2002; 3(3):411-23.
3. Jeansson M, Gawlik A, Anderson G, Li C, Kerjaschki D, Henkelman M, and Quaggin S E. Angiopoietin-1 is essential in mouse vasculature during development and in response to injury. *The Journal of Clinical Investigation*. 2011; 121(6):2278-89.
4. Conroy AL, Glover SJ, Hawkes M, Erdman LK, Seydel KB, Taylor TE, Molyneux ME, and Kain KC. Angiopoietin-2 levels are associated with retinopathy and predict mortality in Malawian children with cerebral malaria: a retrospective case-control study*. *Crit Care Med.* 2012; 40(3):952-9.
5. Vikkula M, Boon LM, Iii KLC, Calvert JT, Diamonti AJ, Goumnerov B, Pasyk KA, Marchuk DA, Warman ML, Cantley LC, et al. Vascular Dysmorphogenesis Caused by an Activating Mutation in the Receptor Tyrosine Kinase TIE2. *Cell*. 1996; 87(7):1181-90.
6. Augustin HG, Young Koh G, Thurston G, and Alitalo K. Control of vascular morphogenesis and homeostasis through the angiopoietin-Tie system. *Nat Rev Mol Cell Biol*. 2009; 10(3):165-77.
7. D'Amico G, Korhonen EA, Waltari M, Saharinen P, Laakkonen P, and Alitalo K. Loss of endothelial Tie1 receptor impairs lymphatic vessel development-brief report. *Arteriosclerosis, thrombosis, and vascular biology*. 2010; 30(2):207-9.
8. Suri C, Jones PF, Patan S, Bartunkova S, Maisonpierre PC, Davis S, Sato TN, and Yancopoulos GD. Requisite Role of Angiopoietin-1, a Ligand for the TIE2 Receptor, during Embryonic Angiogenesis. *Cell*. 1996; 87(7):1171-80.
9. Charles ST, and Hamasaki DI. THe effect of intraocular pressure on the pupil size. *Archives of Ophthalmology*. 1970; 83(6):729-33.
10. John SW, Hagaman JR, MacTaggart TE, Peng L, and Smithes O. Intraocular pressure in inbred mouse strains. *Investigative Ophthalmology & Visual Science*. 1997; 38(1):249-53.
11. Prusky GT, Alam NM, Beekman S, and Douglas RM. Rapid Quantification of Adult and Developing Mouse Spatial Vision Using a Virtual Optomotor System. *Investigative Ophthalmology & Visual Science*. 2004; 45(12): 4611-6.
12. Feng L, Zhao Y, Yoshida M, Chen H, Yang J F, Kim TS, Cang J, Troy JB, and Liu X. Sustained Ocular Hypertension Induces Dendritic Degeneration of Mouse Retinal Ganglion Cells That Depends on Cell Type and Location. *Investigative Ophthalmology & Visual Science*. 2013; 54(2):1106-17.
13. Kendell KR, Quigley HA, Kerrigan LA, Pease ME, and Quigley EN. Primary open-angle glaucoma is not associated with photoreceptor loss. *Investigative Ophthalmology & Visual Science*. 1995; 36(1):200-5.
14. Cuenca N, Pinilla I, Fernandez-Sanchez L, Salinas-Navarro M, Alarcon-Martinez L, Aviles-Trigueros M, de la Villa P, Miralles de Imperial J, Villegas-Perez MP, and Vidal-Sanz M. Changes in the inner and outer retinal layers after acute increase of the intraocular pressure in adult albino Swiss mice. *Exp Eye Res*. 2010; 91(2):273-85.
15. Smith RS, Zabaleta A, Kume T, Savinova OV, Kidson SH, Martin JE, Nishimura DY, Alward WLM, Hogan BLM, and John SWM. Haploinsufficiency of the transcription factors FOXC1 and FOXC2 results in aberrant ocular development. *Human Molecular Genetics*. 2000; 9(7):1021-32.
16. Crowston JG, Aihara M, Lindsey JD, and Weinreb RN. Effect of Latanoprost on Outflow Facility in the Mouse. *Investigative Ophthalmology & Visual Science*. 2004; 45(7):2240-5.
17. Lehmann OJ, Tuft S, Brice G, Smith R, Blixt Å, Bell R, Johansson B, Jordan T, Hitchings RA, Khaw PT, et al. Novel Anterior Segment Phenotypes Resulting from Forkhead Gene Alterations: Evidence for Cross-Species Conservation of Function. *Investigative Ophthalmology & Visual Science*. 2003; 44(6):2627-33.
18. Norrmén C, Ivanov KI, Cheng J, Zangger N, Delorenzi M, Jaquet M, Miura N, Puolakkainen P, Horsley V, Hu J, et al. FOXC2 controls formation and maturation of lymphatic collecting vessels through cooperation with NFATc1. *The Journal of Cell Biology*. 2009; 185(3):439-57.
19. Dellinger M, Hunter R, Bernas M, Gale N, Yancopoulos G, Erickson R, and Witte M. Defective remodeling and maturation of the lymphatic vasculature in Angiopoietin-2 deficient mice. *Developmental Biology*. 2008; 319(2): 309-20.
20. De Val S, Chi NC, Meadows SM, Minovitsky S, Anderson JP, Harris IS, Ehlers ML, Agarwal P, Visel A, Xu SM, et al. Combinatorial regulation of endothelial gene expression by ets and forkhead transcription factors. *Cell.* 2008; 135(6):1053-64.
21. Srinivasan RS, Dillard ME, Lagutin OV, Lin F-J, Tsai S, Tsai M-J, Samokhvalov IM, and Oliver G. Lineage tracing demonstrates the venous origin of the mammalian lymphatic vasculature. *Genes & Development.* 2007; 21(19):2422-32.
22. Witmer AN, van Blijswijk BC, Dai J, Hofman P, Partanen TA, Vrensen GFJM, and Schlingemann RO. VEGFR-3 in adult angiogenesis. *The Journal of Pathology.* 2001; 195(4):490-7.
23. Watanabe Y, Hamanaka T, Takemura T, and Murakami A. Involvement of Platelet Coagulation and Inflammation in the Endothelium of Schlemm's Canal. *Investigative Ophthalmology & Visual Science.* 2010; 51(1):277-83.
24. Truong TN, Li H, Hong Y-K, and Chen L. Novel Characterization and Live Imaging of Schlemm's Canal Expressing Prox-1. *PLoS ONE.* 2014; 9 (5):e98245.
25. Coleman AL, and Miglior S. Risk Factors for Glaucoma Onset and Progression. *Survey of Ophthalmology.* 2008; 53(6, Supplement):S3-S10.
26. Pandey AN, and Sujata S. Study of long term structural and functional changes in medically controlled glaucoma. *International journal of ophthalmology.* 2014; 7(1):128-32.
27. Toris CB, Yablonski ME, Wang YL, and Camras CB. Aqueous humor dynamics in the aging human eye. *Am J Ophthalmol.* 1999; 127(4):407-12.
28. Kim M, Johnston MG, Gupta N, Moore S, and Ylicel YH. A model to measure lymphatic drainage from the eye. *Experimental Eye Research.* 2011; 93(5):586-91.
29. Fatima A, Culver A, Culver F, Liu T, Dietz W H, Thomson B R, Hadjantonakis A-K, Quaggin S E, and Kume T. Murine Notch1 is required for lymphatic vascular morphogenesis during development. *Developmental Dynamics.* 2014.

What is claimed is:

1. A mouse carrying both a conditional Angiopoietin-2 knockout allele and a conditional Angiopoietin-1 knockout allele, wherein the mouse has insufficient drainage pathways in the corneal limbus, including Schlemm's canal, and lymphatic capillaries.

2. The mouse of claim 1, wherein the conditional Angiopoietin-2 knockout allele targets exon 4 of the Angiopoietin-2 gene.

* * * * *